US006468307B1

United States Patent
Baikoff et al.

(10) Patent No.: US 6,468,307 B1
(45) Date of Patent: Oct. 22, 2002

(54) ANTERIOR CHAMBER IMPLANT FOR TREATING THE PHAKIC EYE

(75) Inventors: Georges Baikoff, Marseilles (FR); Laurent Hoffmann, Foothill Ranch, CA (US)

(73) Assignee: Bausch & Lomb Surgical, Inc., Claremont, CA (US)

( * ) Notice: Subject to any disclaimer, the term of this patent is extended or adjusted under 35 U.S.C. 154(b) by 0 days.

(21) Appl. No.: 09/582,473

(22) PCT Filed: Jan. 8, 1999

(86) PCT No.: PCT/IB99/00014

§ 371 (c)(1),
(2), (4) Date: Sep. 20, 2000

(87) PCT Pub. No.: WO99/34752

PCT Pub. Date: Jul. 15, 1999

(30) Foreign Application Priority Data

Jan. 8, 1998 (FR) .......................................... 98 00117

(51) Int. Cl.⁷ .................................................. A61F 2/16
(52) U.S. Cl. ..................................... 623/6.43; 623/6.49
(58) Field of Search ............................... 623/6.38, 6.43, 623/6.44, 6.49

(56) References Cited

U.S. PATENT DOCUMENTS

| 4,442,553 | A | | 4/1984 | Hessburg |
|---|---|---|---|---|
| 4,463,457 | A | | 8/1984 | Kelman |
| 4,585,455 | A | | 4/1986 | Blackmore et al. |
| 6,015,435 | A | * | 1/2000 | Valunin et al. ................ 623/6 |
| 6,152,959 | A | * | 11/2000 | Portney ...................... 623/6.51 |
| 6,171,337 | B1 | * | 1/2001 | Galin ......................... 623/6.11 |
| 6,241,777 | B1 | * | 6/2001 | Kellan ........................ 623/6.51 |

FOREIGN PATENT DOCUMENTS

| EP | 0 346 245 A1 | 12/1989 |
|---|---|---|
| EP | 0 477 109 A1 | 3/1992 |
| EP | 0 563 602 A1 | 10/1993 |
| GB | 2 171 912 A | 9/1986 |

OTHER PUBLICATIONS

Baikoff et al., *Angle–fixated anterior chamber phakik intraocular lens or myopia of –7 to –19 diopters*, Journal of Refractive Surgery, vol. 14, No. 3, May 1998, pp. 282–293, XP002078963.

* cited by examiner

Primary Examiner—David H. Willse
Assistant Examiner—Javier G. Blanco
(74) Attorney, Agent, or Firm—Oliff & Berridge, PLC

(57) ABSTRACT

The invention provides an anterior chamber implant for treating a phakic eye having an optical part connected to loops. The loops have an arc-shaped profile with a double radius of curvature. The radius of curvature of the proximal portion being greater than that of the distal portion.

9 Claims, 3 Drawing Sheets

ANTERIOR CHAMBER IMPLANT FOR TREATING THE PHAKIC EYE

The present invention relates to an anterior chamber ocular implant for treating conditions of the phakic eye, in particular myopia, astigmatism and hypermetropia.

Such an implant consists, in a known manner, of an optical part (lens), generally of circular contour and with a section appropriate for the planned correction (plane, planoconvex, biconvex, planoconcave, biconcave, meniscus, toric); connected to this optical part there is a haptic part which is intended to fix the position of the optical part in the anterior chamber. The haptic part consists of fine and deformable loops which, in use, lodge in the iridocorneal angle.

An implant of the above type, intended for correction of myopia, is shown diagrammatically in FIGS. 1, 2 and 5 appended to the present description, FIG. 1 being a plan view, FIG. 2 a side view, and FIG. 5 a diagrammatic view of the implant according to FIGS. 1 and 2 in position in an eye.

FIG. 1 shows the optical part 1, the connection zone 2 between this optical part and the two loops 3 and 4 which have the general shape of an S, the distal part of each loop having two support feet 5 and 6.

It will be seen in FIG. 2 that the optical part 1 is of the concave type and that the loops 3, 4 are angulated from their proximal part for connection with the optical part 1 towards their distal support part, relative to a vertical support plane A.

This angle α is of the order of 15° and is intended to ensure that the optical part 1 is placed in the anterior chamber of the eye without risk of contact either with the cornea on its front face or with the iris on its rear face.

It will also be seen in FIG. 2 that the distal end of the loops 3 and 4 coincides with the vertical plane A along a relatively important length.

The implant has a width of about 5.5 mm (reference L in FIG. 1) and is inscribed in an envelope curve having a diameter of between 12 mm and 13.5 mm (reference D in FIG. 1). Such an implant is adapted to most shapes and sizes of eyes encountered in patients recovering from refractive surgery.

However, with the earlier models, irritation was found in a not inconsiderable number of cases due to the fact that the distal part of the loops bears on the periphery of the iris.

The object of the present invention is to overcome this disadvantage by very greatly reducing the risk of this distal part of the loops bearing on the periphery of the iris, irrespective of the size of the eye in which it is implanted.

According to the invention, each loop, viewed in profile, has an arc-shaped profile with double radius of curvature in order to place the bearing surface in the iridocorneal angle.

The invention will be better understood with the help of the following description of a nonlimiting embodiment, with reference to FIGS. 3, 4 and 6.

Figure 3:
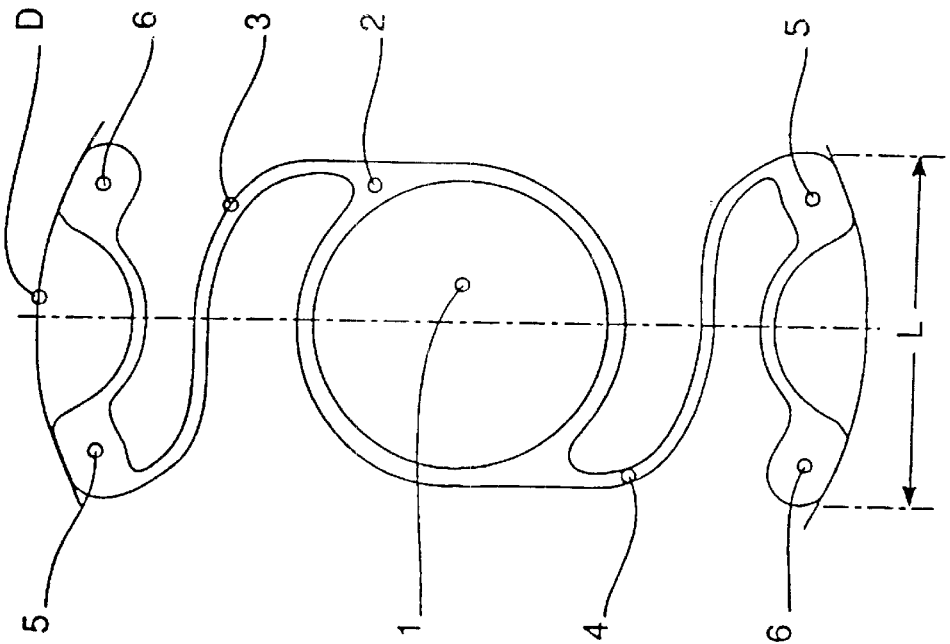
FIG. 3 is a diagrammatic plan view of an anterior chamber myopia implant according to the invention.
Figure 4:
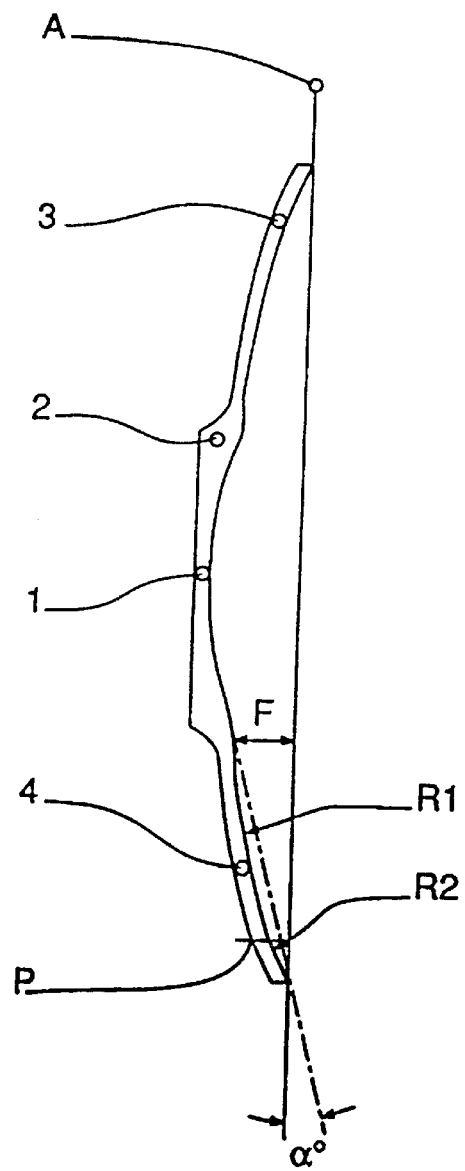
FIG. 4 is a diagrammatic side view of the implant shown in FIG. 3.
Figure 6:
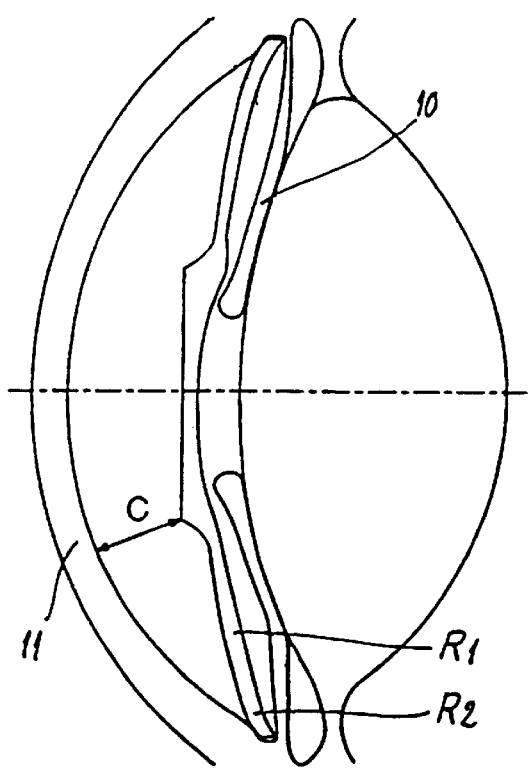

And FIG. 6 is a diagrammatic view of the implant according to FIGS. 3 and 4 in position in the eye.

Figure 1:
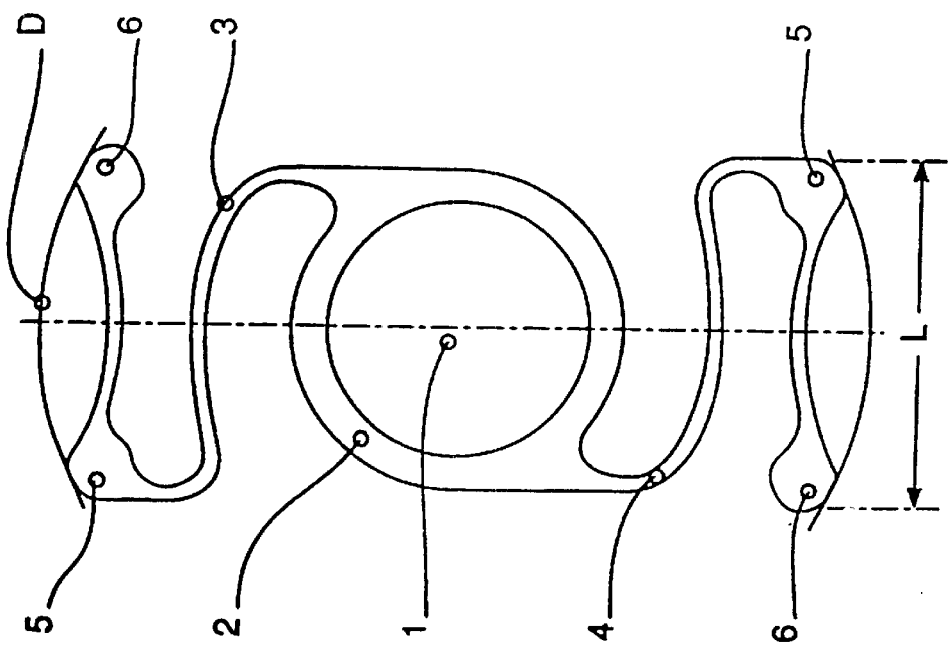
Figure 2:
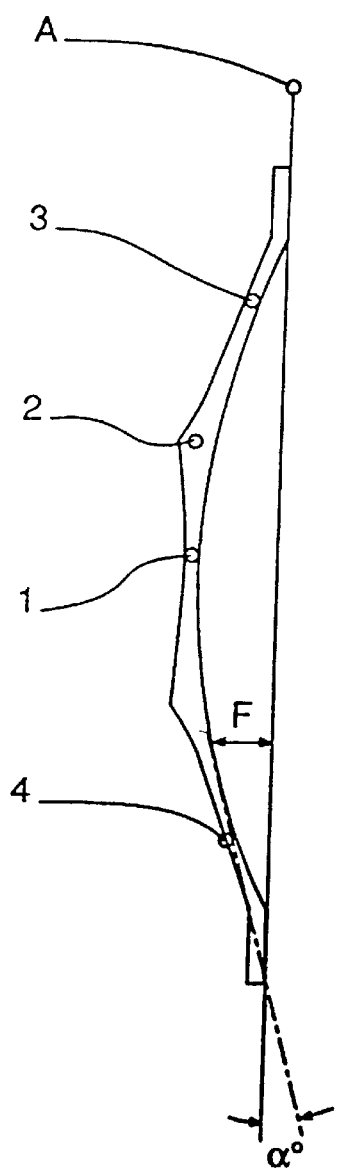

The references for parts which correspond to those of the implant illustrated in FIGS. 1 and 2 are identical. There is an optical part 1, a peripheral connection part 2 and two loops 3 and 4 in the general shape of an S (plan views), of which the distal part has support feet 5 and 6.

Each loop has, in side view according to FIG. 4, an arc-shaped profile with double curvature. The radius of curvature (R1) of the proximal part is greater than that of the distal part (R2). The point of passage from one radius of curvature to the other is situated (cf. reference P in FIG. 4) at a distance from the distal end of the loop in question, approximately equal to quarter the height of the said loop, in a direction parallel to the support plane A.

The general angulation of the loop relative to the support plane A is between 13.5° and 16° and is preferably 15.12° (angle α in FIG. 4) for an implant with an envelope curve of 12.5 mm.

The value of the radii of curvature is between 10 and 35 mm for the proximal part (R1) and 2.5 mm for the distal part (R2).

With these configurations, the head of the loop (reference F in FIG. 4) will be situated approximately 1 mm from the support plane A, and the point of the optical part nearest to the cornea will be situated at 1.62 mm (reference c in FIG. 6). This guarantees that the deformations of the loops, secondary to those of the eyeball, do not risk causing contact of the implant with the cornea or with the iris.

The arc shape with double radius of curvature ensures that the loops will bear only on the relatively strong structures of the iridocorneal angle (scleral spur, trabecula).

Figure 5:
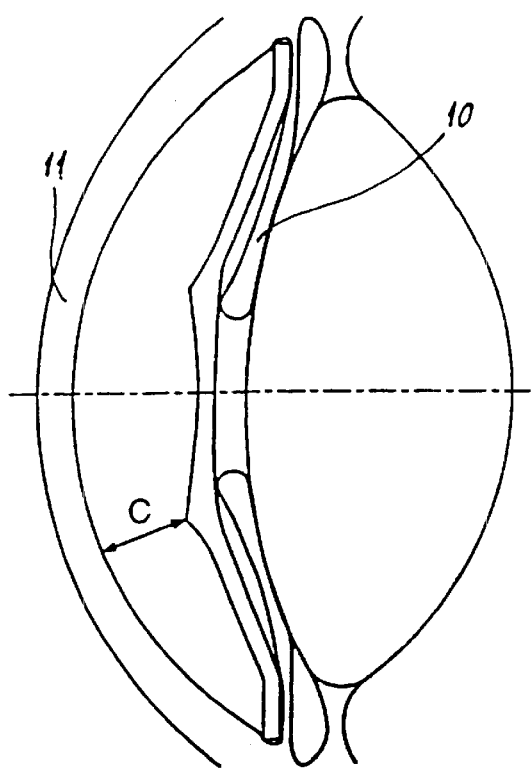

More precisely, according to FIG. 6, and in contrast to FIG. 5:

the proximal part of each loop, with large radius of curvature (R1), is almost parallel to the optical plane; it is situated as far as possible from the iris, in order to allow pupillary movement without contact between the loop and the iris;

the distal part of each loop, with small radius of curvature (R2), joins the proximal part practically in the site of implantation of the loops, corresponding to the angle of the anterior chamber;

each loop is thus placed in a mid position between the iris 10 and the corneal endothelium 11;

the support surface of each loop in the iridocorneal angle remains limited; practically all contact between the distal part of each loop and the iris is prevented, thereby limiting any inflammatory reaction of the latter.

An embodiment of an implant has been described above in which the haptic part comprises two loops, but it goes without saying that the present invention is applicable to any anterior chamber implant for treating the phakic eye, irrespective of the number of loops of its haptic part.

What is claimed is:

1. Anterior chamber implant for treating the phakic eye, comprising an optical part (1) connected to loops (3, 4), characterized in that, viewed in profile, each loop has an arc-shaped profile with double radius of curvature, the radius of curvature (R1) of the proximal part being greater than that (R2) of the distal part.

2. Implant according to claim 1, characterized in that the point of passage between the two radii of curvature (R1) and (R2) is situated at a distance from the distal end of the loop approximately equal to quarter the height of the loop in a direction parallel to the vertical plane A.

3. Implant according to claim 2, characterized in that a general angulation (α) of a loop is between 13.5° and 16° relative to the support plane A.

4. Implant according to claim 2, characterized in that the value of the radii of curvature is:

R1: $\geq$ 10 mm $\geq$ 35 mm

R2: 2.5 mm.

5. Implant according to claim 1, characterized in that a general angulation ($\alpha$) of a loop is between 13.5° and 16° relative to a vertical support plane A.

6. Implant according to claim 5, characterized in that the angulation of a loop is 15.12° for an implant with an envelope curve of 12.5 mm.

7. Implant according to claim 6, characterized in that the value of the radii of curvature is:

R1: $\geqq 10$ mm $\geqq 35$ mm

R2: 2.5 mm.

8. Implant according to claim 5, characterized in that the value of the radii of curvature is:

R1: $\geqq 10$ mm $\geqq 35$ mm

R2: 2.5 mm.

9. Implant according to claim 1, characterized in that the value of the radii of curvature is:

R1: $\geqq 10$ mm $\geqq 35$ mm

R2: 2.5 mm.

* * * * *